United States Patent [19]

Cordon et al.

[11] 4,439,416

[45] Mar. 27, 1984

[54] SELF-HEATING SHAVING COMPOSITION

[75] Inventors: Martin Cordon, Somerset; Alan Dillarstone, Highland Park, both of N.J.

[73] Assignee: Colgate - Palmolive Company, New York, N.Y.

[21] Appl. No.: 17,777

[22] Filed: Mar. 5, 1979

Related U.S. Application Data

[63] Continuation of Ser. No. 344,314, Mar. 23, 1973, abandoned, which is a continuation of Ser. No. 56,082, Jun. 22, 1970, abandoned, which is a continuation of Ser. No. 560,140, Jun. 24, 1966, abandoned.

[51] Int. Cl.³ .............................................. A61K 7/15
[52] U.S. Cl. ........................................ 424/47; 424/73
[58] Field of Search ................................... 424/73, 47

[56] References Cited

U.S. PATENT DOCUMENTS 3,338,403  8/1967  Carlson .................................. 424/47
3,341,418  9/1967  Moses et al. ........................... 424/47

OTHER PUBLICATIONS

Bragg et al., J. Chem. Soc., (Condon), 1957, pp. 4343–4352.
Burns, Dissertation Abs., (1964), vol. 24, No. 10, pp. 3969–3970.
Stockmayer et al., Chem. Abs., (1961), vol. 55, pp. 2499.

*Primary Examiner*—Dale R. Ore
*Attorney, Agent, or Firm*—Herbert S. Sylvester; Murray M. Grill; Norman Blumenkopf

[57] ABSTRACT

The present invention relates to a cosmetic preparation which is particularly effective for providing a cosmetic product that is heated at time of use by the heat of an exothermic reaction, and a process for carrying out such heating.

5 Claims, 3 Drawing Figures

SELF-HEATING SHAVING COMPOSITION

This is a continuation of application Ser. No. 344,314 filed Mar. 23, 1973, now abandoned which is in turn a continuation of application Ser. No. 56,082 filed June 22, 1970 and now abandoned, which was in turn a continuation application of Ser. No. 560,140 filed June 24, 1966 and also now abandoned.

The present invention relates to a cosmetic preparation which is particularly effective for providing a cosmetic product that is heated at time of use by the heat of an exothermic reaction, and a process for carrying out such heating, as hereinafter described and claimed.

In accordance with the present invention, it has been found that a self-heating cosmetic preparation composed of at least two discrete parts particularly suitable for providing a heated cosmetic product at time of use has one part comprising a hydride and a second part comprising a reducible material adapted to react exothermically with said hydride on contact therewith, and a cosmetic base in which one of said parts is incorporated, whereby at time of use the parts combine and interact exothermically to issue as self-heated cosmetic preparation.

A preferred embodiment relates to a self-heating shaving cream preparation composed of at least two parts adapted to be dispensed as a pressure-propelled heated shaving cream at time of use, one part comprising a liquid medium containing a hydride and the second part comprising a shaving cream base having incorporated therein a reducible material adapted to react exothermically with said hydride on contact therewith, each of said parts adapted to be dispensed from pressure-tight dispensers having a common discharge means for simultaneous discharging and commingling said parts on activation thereof, whereby on such activation said parts combine and interact exothermically to issue as a pressure-propelled self-heated shaving cream ready for use.

The cosmetic preparations of the present invention are highly advantageous not only in that they provide heated cosmetic compositions, but also in that the cosmetic compositions are self-heating for providing heated cosmetic products at the time of use without the necessity of any separate heating devices. Accordingly, heating of the compositions by electrical devices, hot water, or hot air is not required since the ingredients combine and interact exothermically to provide a self-heated cosmetic product ready for use. In addition, separate heating devices give immediate heat to products with subsequent cooling thereafter, whereas the heat of the exothermic reaction enables the product to become progressively warmer and the heat is sustained over a period of time. The self-heating cosmetic preparation is composed of at least two discrete parts so that the ingredients which react exothermically are reacted only at the desired time, i.e. just prior to use. As a result, the consumer can utilize these preparations conveniently by the simultaneous discharge of the parts for heating, and the preparations are such that the parts will be combined and interact exothermically in constant proportions.

The compositions of the present invention are characterized by being composed of at least two discrete parts particularly suitable for providing heated cosmetic products at time of use by means of an exothermic reaction. One part contains a substantially stable hydride, which is preferably employed in a liquid medium, and the second part contains a reducible material adapted to react exothermically with the hydride on contact therewith. A cosmetic base may be incorporated in either of these parts. When present in a liquid medium, the hydride may be dissolved in an aqueous alkaline solution, a non-aqueous solution (i.e. solubilized with a suitable solvent) or the hydride may be suspended as a solid in a non-solvent. In these liquid media, the hydride is sufficiently stable that no exothermic reaction takes place until it is contacted with the reducible material. Accordingly, while the compositions are composed of at least two parts, the formulation of the products is such that when a portion of the hydride part and a portion of the reducible material part are combined there is a rapid, exothermic chemical reaction during mixing and a heated product is provided. Thus, in the interaction of the selected hydride and selected reducible material, the reducing reaction is "in situ", rapid, and the by-products will be tolerated by the skin.

Since a heated product is desired at the time of use, the heat producing parts are kept separate during storage and allowed to come in contact only when a warm cosmetic preparation is desired for use. Preferably, the parts are packaged in separate pressure-tight dispensers containing a propellant and provided with a common discharge device for simultaneously discharging and commingling portions of each part on activation thereof, whereby on such activation the parts combine and interact exothermically to issue as a self-heated cosmetic product ready for use.

The hydride employed in the self-heating cosmetic preparations of the present invention provides one of the selective reagents for producing a rapid, in situ heat of reaction to be utilized for a self-heated product. Accordingly, the hydrides to be employed are the hydride compounds which are characterized by their being satisfactory reducing agents for the reducible materials and their by-product not having any established toxicity for the skin. By satisfactory reducing agent, it is meant that the reduction with the hydride will be non-explosive, non-flammable and evolve heat. Typical hydrides are alkali metal and alkaline earth metal borohydrides, alkali metal and alkaline earth metal aluminum hydrides, ammonium borohydrides and quaternary ammonium borohydrides. Among the hydrides it is preferred to employ the alkali metal borohydrides such as sodium and potassium borohydrides. Such borohydrides contribute to making satisfactory cosmetic products for application to human skin since their by-products are well tolerated by the skin. Other suitable hydrides include commercial borohydrides such as alkaline earth metal borohydrides typified by calcium borohydride; ammonium borohydride; quaternary ammonium borohydrides such as cetyl trimethylammonium borohydride and tricapryl methyl ammonium borohydride; and commercial hydrides such as alkali metal aluminum hydrides typified by sodium aluminum hydride and alkaline earth metal aluminum hydrides such as calcium aluminum hydride.

The hydride is preferably in a liquid carrier in order to facilitate the commingling of the hydride with the part containing the reducible material for a substantially complete reaction. However, it is to be understood that although it is preferred to employ a liquid carrier, the hydride can be used as a dry, solid material in granular form.

The liquid medium for the hydride is a selected one since hydrides will release hydrogen in the presence of water through the gradual decomposition of the compound. The liquid medium is characterized in that the hydride is readily dissolved by the liquid medium or the hydride is suspended in a non-solvent liquid carrier and in either case the hydride is sufficiently stable in the selected medium so that the hydride does not substantially decompose prior to contact with the reducible material. Preferably the hydride is stably suspended in a non-solvent liquid carrier. The non-solvents useful in providing a stable suspension of hydride particles therein are any of those which do not dissolve the hydride and have the ability to provide a dispersion of undissolved solid particles in a liquid medium, the dispersion being of such nature that the solid particles do not settle and cake so that each small portion of the suspension will have practically the same composition. However, the non-solvents should be compatible with cosmetic preparations and those looked upon as suitable components for cosmetic compositions are preferred. Suitable non-solvents are hydrocarbon materials such as liquefied, paraffinic hydrocarbons, e.g. mineral or paraffin oil, liquid petrolatum or white mineral oil and similar mixtures of liquid hydrocarbons obtained from petroleum. While the particle size of the finely divided hydride particles is not critical by itself, it can influence the stability of the suspension in the non-solvent liquid carrier or the stability of the suspension in a pressure propelled system and the type of valve for the dispenser. Generally, the particle size of the hydrides will range from about 10 microns to about 100 microns although coarser or finer materials may be used. The finer particles will be readily suspended and dispensed in a pressure propelled system whereas the larger particle sizes must be small enough so that they can be effectively suspended and can be dispensed without clogging the valve opening upon release of the pressure propelled system. Preferably, for use in conventional aerosol dispensers the hydrides are of a particle size less than about 45 microns.

Suitable liquid media for use in dissolving the hydrides are aqueous alkaline solutions such as water-alkali metal hydroxide solutions; dimethyl ethers of mono-, di-, tri- and tetra-ethylene glycols such as dimethyl ether of triethylene glycol, dimethyl ether of tetra-ethylene glycol; alcohols having at least 3 carbon atoms such as octyl alcohol, isopropanol, tertiary butyl alcohol; amines such as isopropyl amine and amides such as dimethyl formamide. The particular type of liquid media is selected according to the particular hydride and its solubility properties and stability in the media.

The problems peculiar to the liquid medium having hydride particles suspended therein are similar for a dry hydride powder system. Accordingly, the dry granular hydride should be stored in a sealed container prior to commingling with the reducible material in order to avoid deterioration such as through contact with atmospheric moisture. Aerosols in powder form are well known in the art and the hydride powder can be dispensed from a pressurized dispenser through the use of selected valves and formulations. As the powder will not be in a liquid carrier, the hydride powders are packed with propellants which will not dissolve the hydride powder because the powders must remain particulate and non-agglomerating. The particle size of these hydride particles may also range from about 10 microns to about 100 microns with a particle size less than about 45 microns being preferable.

The reducible material employed in this invention is adapted to react exothermically on contact with the hydride. Thus, the reducible material is the other selective reagent for producing a rapid, in situ heat of reaction to provide a self-heated product. The selected reducible material is characterized in that it is readily reduced by the selected hydride and the reduction of the material by the hydride is in situ, rapid, and extremely exothermic so that the temperature of the cosmetic preparation is not raised prior to their combination but just before usage of the product. Any suitable material which is reduced by the hydride with heat of reaction and does not provide a reaction product with any toxicity for the skin may be used. Typical suitable reducible materials are aldehydes such as glyceraldehyde, hexanal, crotonaldehyde, 2-methylpropenal, benzaldehyde, furfural; ketones such as acetone, dihydroxyacetone, 2,4 pentanedione; peroxides such as acetyl peroxide and benzoyl peroxide; acid chlorides such as crotonyl chloride, benzoyl chloride; and sulfoxides such as dimethyl sulfoxide.

The cosmetic base is preferably a shaving cream base in order to provide a self-heating shaving cream preparation. It is to be understood that although a shaving cream base is preferable and used for purpose of illustration, other cosmetic bases can be used, as will be readily apparent to those skilled in the art. Other typical cosmetic bases are waterless skin cleansers, hand lotions, body lotions, and the like. Of course, any cosmetic base employed in this invention should be stable in the presence of the hydrides and reducible materials as well as compatible with these materials when a heated product is provided. Thus, such cosmetic bases should be stable and non-reactive with the other ingredients in the system.

The shaving cream base may be any of the numerous types of detergent creams particularly adapted for use as a shaving cream preparation which are well known in the art. These preparations are, in general, soaps, i.e. a higher fatty acid soap which is the reaction product of a higher fatty acid and a soap-forming base. These soaps are the principal deterging or cleansing agent for the shaving preparations. Suitable higher fatty acids are those containing 10 to 18 carbon atoms such as lauric, myristic, palmitic, stearic and oleic acids, and mixed fatty acids obtained from coconut, olive, palm, palm kernel and like fats and oils. Suitable soap-forming bases are inorganic bases such as alkali metal hydroxides, e.g. sodium or potassium hydroxide, or ammonia and organic bases such as amines, e.g. monoethanolamine, triethanolamine, isopropanolamine and the like. Besides these classic saponification products, the shaving cream compositions will have an aqueous solvent medium such as water for the soap. Minor proportions of optional ingredients such as perfumes and skin fresheners or lather stabilizers or the like such as glycerine, lanolin, lecithin, borax, coconut oil, fatty amides, fatty acids, alcohols, etc. may be added to the preparation to provide a shaving cream base in accordance with the present invention.

In the self-heating cosmetic compositions adapted to be dispensed as a pressure-propelled product, the propellant used in the pressurized container can vary widely. Any propellant material generally employed in pressurized dispensing containers is suitable in the practice of the present invention, although the liquefied gases are preferable. Among those gases are the polyhalogenated lower hydrocarbons such as chlorinated and fluorinated methanes, ethanes and higher homologues, e.g. monochlorodifluoromethane, monochlorodifluoroethane, dichlorodifluoromethane, dichlorodifluoroethane, trichloromonofluoromethane and dichlorotetrafluoroethane; and the lower hydrocarbons such as propane, butane and isobutane. Compressed gases such as nitrogen, oxygen, nitrous oxide and carbon dioxide may also find use. In some instances it may be desirable to use a combination of two or more of the liquefied normally gaseous materials as a propellant in order to achieve a suitable pressure within the container and impart the desired properties of stability, propellancy, ease of delivery, etc. to the cosmetic preparations.

The amount of propellant may be varied depending upon the properties desired. In general, it need be present in an amount sufficient to propel or to eject satisfactorily the contents of the container. It has been found, however, that at least 1% and preferably 2 to 5% propellant, by weight of the total composition in the container, should be used although higher amounts may be employed if desired, e.g. up to about 10%.

Other substances may be added to the present compositions for special effects provided the character of the product is not substantially adversely affected. Thus, viscosity adjusting agents such as paraffin wax, carboxymethyl cellulose; suspending agents such as finely-divided, anhydrous silica; and pH adjusting agents such as sodium hydroxide, ethanolamines and carboxylic acids such as citric acid may be employed. For the provision of improved and stable foam in pressurized self-heating shaving cream preparations, foam stabilizers such as higher fatty acid amides of a lower alkylolamine and ethoxylated higher fatty acid alkanolamides are used. Typical higher fatty acid amides of a lower alkylolamine (well known in the art as higher fatty acid alkylolamides) are mono- and diethanolamide of coconut oil fatty acids, diethanolamide of mixed lauric-myristic acids, diethanolamide of mixed lauric-coconut oil acids, and the diethanolamide of tallow fatty acids. Typical ethoxylated higher fatty acid alkanolamides are exemplified by the condensation product of monoethanolamide of coconut oil fatty acids with two moles of ethylene oxide, the condensation product of lauric monoethanolamide with two moles of ethylene oxide, and the condensation product of the monoethanolamide of coconut oil fatty acids with 5 moles of ethylene oxide. Besides these higher fatty acid alkanolamides and higher fatty acid polyethoxylated alkanolamides containing up to 6 ethylene oxide groups in the polyethoxy portion, the higher fatty acid radical of said amides having about 12 to 18 carbon atoms, other known foam stabilizers may also be found useful in the present invention.

In providing the self-heating preparation of the present invention, the hydride and reducible materials adapted to react exothermically with the hydride are controlled in order to have an effective amount of reactants for a rapid rate of reaction. Additionally the ratio of the hydride to the reducible material is controlled to help insure completeness of reaction. For example, sodium borohydride is slightly irritating to the skin, but its reaction product, sodium borate, is not. In general, the ratio of hydride to reducible material may be from about 2:1 to about 1:2 on an equivalent basis. Preferably, the reactants are used in substantially chemical equivalent quantities, i.e. a ratio of about 1:1 on an equivalent basis.

The period of time to form the heated product is variable and depends upon the particular reactants. In general, the oxidation-reduction reaction between the hydride and the reducible material begins when the ingredients are commingled and the product becomes progressively warmer during the exothermic reaction, i.e. the liberation of heat can last up to about 60 seconds. Since the reaction is an extremely exothermic one, i.e. gives out a lot of heat from a very small quantity of material, the heat is sustained over a period of time from about 60 to about 180 seconds. It is unnecessary to use any other device for heating the product in view of the fact that these are relatively high energy reactions, i.e. provide heat greater than about 10 kilogram-calories per mole of hydride. While in many cases the rate of reduction may be so rapid as to make accurate measurement impossible, heat generated within the range from about 10 to about 200 kilogram-calories per mole is adequate.

When preparing the self-heating cosmetic preparations, the hydride-containing portion and the reducible material-containing portion are prepared separately and only combined when a heated product is desired for use. The hydride-containing media can be prepared in accordance with a variety of procedures. One method by which a hydride may be placed in a liquid medium is by dissolving the hydride in a suitable solvent medium at room temperature with stirring. When hydrides which react with water (i.e. those dissolved hydrides which react very slowly with water to yield hydrogen) are employed in an aqueous medium, or a solvent medium containing water, the hydride solution should be stabilized toward hydrolysis. Thus, a hydrolysis inhibitor such as sodium hydroxide is added to the aqueous-hydride solutions with stirring to prevent hydrolysis. However, for the preferred self-heating shaving cream preparations, the hydride is added in particulate form to a non-solvent medium with stirring to form a stable suspension. For use in pressure-propelled compositions, the hydride should be in finely divided form prior to suspension in the non-solvent medium. If the hydride is not suitable in finely divided form (e.g. particle size less than about 45 microns), the hydride can be finely divided by ball-milling, such as by using one-half inch porcelain balls. Other ingredients such as perfumes, colorants, foam stabilizers, suspending agents and the like are thereafter incorporated in the liquid medium.

While either the hydride portion or the reducible material may be incorporated in a cosmetic composition, the presently preferred procedure is to incorporate the reducible material in the cosmetic composition. Thus, the physical character of the presently preferred reducible material portion, e.g. a shaving cream base with the reducible material incorporated therein, is that of a stable aqueous solution. The term "stable aqueous solution" as used herein means that the reducible material does not substantially react with the shave cream base and the portion has satisfactory stability.

Pressurized hydride portions and pressurized reducible material portions may be prepared in any suitable manner. In general, the respective portion is placed in a container and pressurized with propellant.

In packaging the self-heating cosmetic products, the hydride-containing part and the reducible material part are kept as separate portions. Each portion may be placed in either conventional glass bottles, plastic squeeze containers or pressurized "aerosol" containers. Preferably, they are packaged in separate pressurized "aerosol" containers having a common discharge device in opposed axial disposition or disposed in a side-by-side relationship. Additionally, they may be placed into a container divided into two separate compartments by a common wall extending the length of the container and having a common exit.

A typical two-container dispensing system is shown in the drawings in which.

Figure 1:
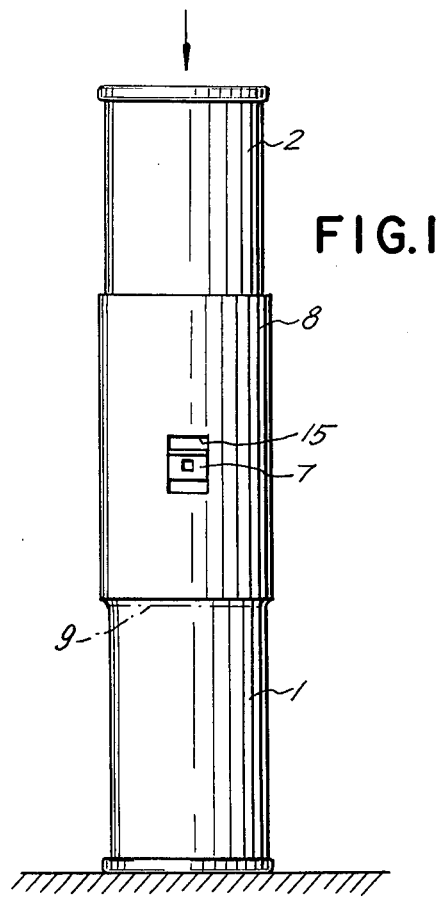
FIG. 1 is a front elevational view showing the typical dispensing apparatus.
Figure 2:
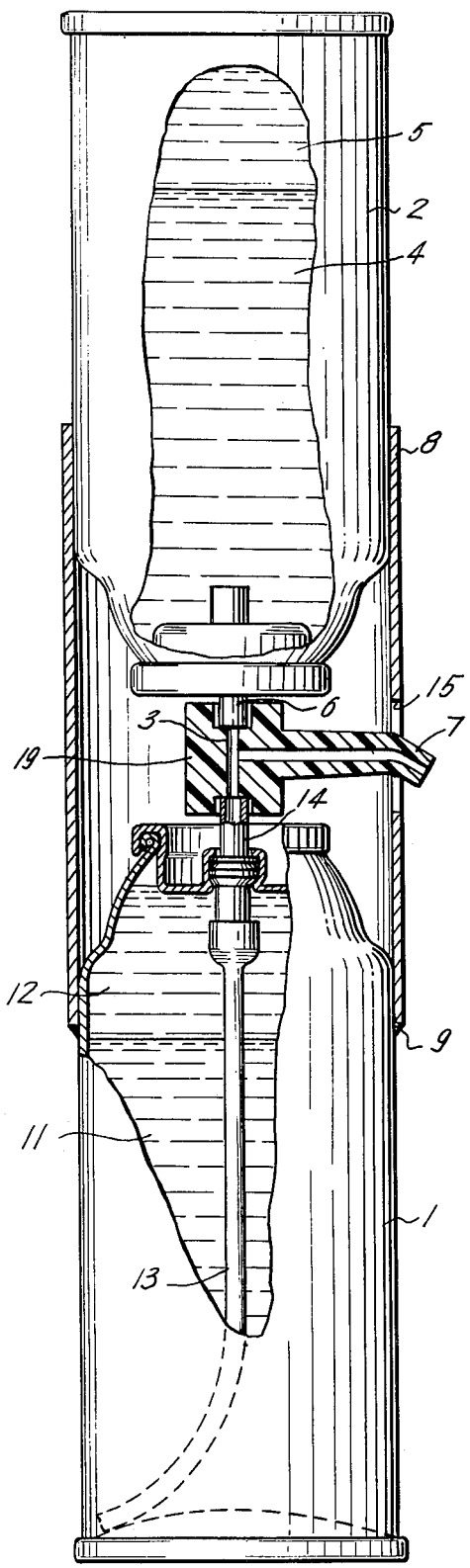
FIG. 2 is a partially cut-away side elevation of this dispensing apparatus.

As shown in FIGS. 1 and 2, the two cylindrical pressure-tight dispensers 1 and 2 are connected to a discharge device 19 having a common discharge chamber 3 and a discharge spout 7 and held in an opposed axial disposition by a casing or sleeve 8. The sleeve 8 is generally circular in configuration and is telescopically mounted so that it encircles the discharging device and adjacent portions of the dispensers 1 and 2. An opening 15 is provided for the spout 7 and the lower edge 9 of the sleeve 8 is secured to the upper portion of the dispenser 1. The sleeve, as well as the dispensers, can be fabricated from a wide variety of material such as metal, plastic, ceramic materials and the like. Thus, the lower edge 9 is secured to the wall of the dispenser 1 by soldering, brazing, welding, fusing or the like.

The pressure-tight dispenser 2 contains a hydride-liquid medium 4 which is pressurized by a liquefied, normally gaseous, propellant material 5. The pressure of the propellant material is adapted to push the hydride containing—liquid medium 4 through an outlet 6 into the discharge chamber 3 and out the discharge nozzle 7.

The pressure-tight dispenser 1 contains a reducible material 11 which is incorporated in a cosmetic base and a propellant material 12. The pressure of the propellant 40 is adapted to drive the reducible material 11 through the dip tube 13 and the outlet 14 into the discharge chamber 3 and out the discharge nozzle 7.

It will be noted that pressure-tight dispenser 1 employs dip tube 13 which extends to the bottom of the container and near the side wall thereof and is secured at its upper end to outlet 14. With the use of a dip tube, the contents can be discharged from pressure-tight dispenser 1 in its normal vertical position. However, since pressure-tight dispenser 2, as shown in the drawings, is designed to be held in an inverted position a dip tube is not required, i.e. a valve assembly without a dip tube may be used satisfactorily. Of course, it is to be understood that acceptable pressurized compositions can be designed and produced for each of the pressure-tight dispensers with a variety of valves having discharge orifices with varying discharge areas and with various dimensions of the dip tubes, when employed.

Figure 3:
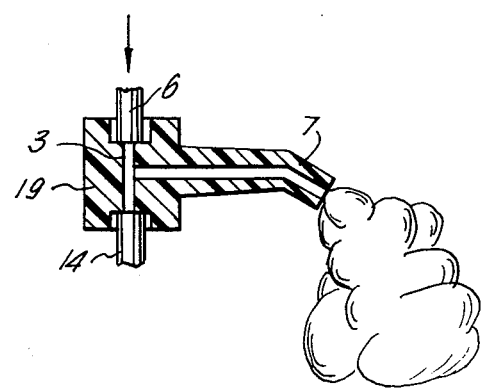
FIG. 3 is a plan of the discharge means when contents are being discharged.

In the operation of the illustrative device, vertical pressure is applied to the pressure-tight dispenser 2 (as indicated by the arrow in FIG. 1) whereby the dispensers 1 and 2 are slidably actuated so that the materials are simultaneously discharged from each dispenser into the discharge chamber 3 and out the discharge nozzle 7 (as shown in FIG. 3). The opening 15 in the sleeve 8 provides an outlet for the discharge nozzle 7 and is of sufficient size to enable vertical displacement of the nozzle 7. Proper execution of said simultaneous discharge permits commingling of the materials before the final composition leaves the nozzle 7. This enables the reducible material to react exothermically with the hydride and a heated product is provided ready for use.

Pressurized containers with valve outlets are generally well known in the art of packaging liquids in pressurized containers and those illustrated are merely exemplary. The design and construction of the two-container dispensing apparatus may likewise be varied.

In preparing and packaging the self-heating cosmetic preparations, the amounts of ingredients other than the ratio of the hydride to the reducible material are not critical. Thus, as recognized by those skilled in the art, in the hydride containing portion the liquid medium will have a minor proportion of hydride and a major proportion of liquid carrier, e.g. solvent and/or suspending agent. Similarly, in the reducible material portion the shaving cream base is the major proportion of the composition and the reducible material is a minor porportion incorporated therein. Although the pH of the final preparation is not of critical importance, it is well known that high pH solutions (about about 11) tend to have an irritating effect upon the skin. The normal pH of the final preparation will have an adjusted pH in the range of the cosmetic base, e.g. the heated shave cream preparations can have a pH range from about 7 to about 11 and preferably from about 7 to about 9.

The following examples are given to illustrate the present invention more fully but are not to be regarded as limiting the scope of the invention. All amounts and percentages given in the specification and claims are by weight unless otherwise indicated.

EXAMPLE I

The following hydride-containing part (A) and reducible material-containing part (B) produce effective self-heating shaving cream preparations:

| (A) | Parts by Weight | (B) | Parts by Weight |
| --- | --- | --- | --- |
| Water | 18.0 | Glyceraldehyde | 33.0 |
| Sodium Hydroxide | 0.4 | (40% aqueous | |
| Sodium Borohydride | 9.0 | solution) | |
| Lauric-coconut | 6.0 | Citric Acid | 0.6 |
| diethanolamide | | Shaving Cream | 66.4 |
| Paraffin Oil | 66.6 | Base* | 100.0 |
| | 100.0 | | |

*Shaving Cream Base contains 83% water, 7% stearic acid, 3% potassium hydroxide, 1% sodium hydroxide, 1% coconut oil fatty acids, and balance being optional ingredients (perfume, coconut oil, glycerine, lauric-myristic diethanolamide).

Part (A) is prepared by first dissolving the sodium borohydride in the water in the presence of the sodium hydroxide hydrolysis inhibitor at room temperature with gentle stirring. Thereafter, the lauric-coconut diethanolamide and paraffin oil are added thereto with stirring.

Part (B) is prepared by adding to the shaving cream base the aqueous solution of glyceraldehyde and the citric acid at room temperature with gentle stirring. The citric acid is present in an amount sufficient to adjust the pH of the solution to below 11, i.e. in an amount sufficient to prevent the formation of a too highly alkaline system.

In assembling a two-container dispenser system to provide a self-heated shaving product as shown in the drawing, 150 grams of part (A) are added to dispenser 2 which is subsequently sealed and thereafter 4.5 grams of an 87% isobutane/13% propane propellant is introduced into the container through the valve. In a similar fashion, dispenser 1 is loaded with 150 grams of part (B) and 4.5 grams of an 87% isobutane/13% propellant.

The discharge device 19 is mounted on dispenser 1 by the discharge chamber 3 receiving the outlet 14 in a close fit. Pressure-tight dispenser 2 is affixed to the discharge device through the close fit of the outlet 6 into the diametrically opposed end of the discharge chamber 3 whereby the dispenser 2 is in an inverted position. Thereafter the casing 8 is mounted and the pressure-tight dispensers 1 and 2 are held in opposed axial disposition. In normal operation, pressure is applied downwardly on the inverted pressure-tight dispenser 2 whereby parts (A) and (B) are simultaneously discharged into the dispensing chamber 3 of the dispensing device. While in dispensing chamber 3 parts (A) and (B) are commingled whereby the parts combine and the sodium borohydride of (A) and the glyceraldehyde of (B) interact exothermically so that the shaving cream is heated and the preparation issues from the discharge nozzle 7 in the form of a heated shaving cream ready for use.

EXAMPLE II

The procedure of Example I is repeated except that in Part (A) 10 parts of sodium borohydride are dissolved in 90 parts of triethylene glycol dimethyl ether. The product of the example also issues as a heated shaving cream ready for use.

EXAMPLE III

The procedure of Example I is repeated except that in Part (B) 7 parts dihydroxyacetone, 7 parts acetone and 0.7 part citric acid are added to 85.3 parts shaving cream base. This example also provides a heated shaving cream product ready for use.

EXAMPLE IV

Another effective self-heating shaving cream preparation is produced by the following borohydride-containing part (A) and reducible material-containing part (B):

| (A) | Parts by Weight | (B) | Parts by Weight |
|---|---|---|---|
| Sodium borohydride | 9.0 | Glyceraldehyde (40% aqueous solution) | 30.0 |
| Paraffin oil (heavy) | 85.0 | Lauric-coconut diethanolamide | 4.0 |
| Paraffin wax | 5.0 | Citric Acid | 0.4 |
| Cab-o-sil* | 1.0 | Shaving Cream | 65.6 |
|  | 100.0 | Base of Example I | 100.0 |

*Finely divided, anhydrous silica

Part (A) is a stable suspension of sodium borohydride in a non-solvent liquid medium. Commercial sodium borohydride having a particle size of about 100 microns is ball-milled in the presence of the commercial anhydrous silica (finely divided) to provide sodium borohydride particles of less than about 45 microns. The ball-milling of the sodium borohydride is done in the presence of the anhydrous silica which serves as a drying agent to prevent any decomposition of the borohydride as well as a suspending agent. To a commercial heavy-grade paraffin oil, there is added the particulate sodium borohydride mixture and paraffin wax at room temperature with stirring.

The preparation of part (B) is similar to the procedure of Example I in that the glyceraldehyde, citric acid and lauric-coconut diethanolamide are added to the shaving cream base.

After the preparation of parts (A) and (B), 50 grams of (A) are placed in a 2 ounce aerosol dispenser and pressurized with 1.5 grams of n-butane. 150 grams of (B) are placed in a 6 ounce aerosol dispenser and pressurized with 4.5 grams of 87% isobutane and/13% propane propellant. Each dispenser is connected to a common discharge device as in Example I whereby the smaller dispenser is in the inverted position.

In the smaller, inverted container, the use of n-butane lowers the vapor pressure of the container while the inclusion of paraffin wax raises the viscosity of the suspension so that in normal operation, i.e. when pressure is applied as in Example I, the ratio of the release of the contents of the inverted container to the contents of the second container is 1:3. However, the ratio of sodium borohydride to glyceraldehyde is about 1:1 on an equivalent basis.

The product of this example dispenses from the discharge nozzle as a heated shaving cream ready for use.

EXAMPLE V

The procedure described in Example IV is repeated using potassium borohydride in place of sodium borohydride to provide a stable suspension of potassium borohydride in heavy paraffin oil. After packaging in aerosol dispensers and assembling a dispenser system, the product dispenses as a heated shaving cream ready for use. Similar experiments relating to self-heating shaving cream preparations are carried out using sodium borohydride, ammonium borohydride, cetyl trimethylammonium borohydride, sodium aluminum hydride, or calcium aluminum hydride portion with an aldehyde or a ketone portion to react exothermically on combination thereof to provide a heated shaving product ready for use.

As indicated in the preceding examples, the preparations herein disclosed are adapted for use in conventional aerosol containers now in commercial use. Inasmuch as these containers can be made from a wide variety of materials, e.g. aluminum, steel, tinplate and the like, certain chemical reactions may occur between the said materials and the contained products. In order to avoid any undesirable results, it may be desirable to either coat the inside of the container with a corrosion resistant coating such as a suitable lacquer, or incorporate a corrosion inhibitor, such as silicate, phosphate, etc., in the contained product.

Although the present invention has been described with reference to particular embodiments and examples, it will be apparent to those skilled in the art that variation and modifications of this invention can be made and that equivalents can be substituted therefor without departing from the principles and true spirit of the invention as defined in the appended claims.

What is claimed is:

1. A package for dispensing a self-heating, self-foaming shaving cream composition, said package having two compartments for separate storage of ingredients of said composition from which the ingredients are adapted to be dispensed for mixing with each other with the generation of heat, the first compartment having therein about 9% sodium borohydride, about 85% heavy paraffin oil, about 5% paraffin wax and about 1% finely divided anhydrous silica, the borohydride being of a particle size of about 100 microns and the silica being less than about 45 microns; and, in the other compartment about 12% of glyceraldehyde, about 18% water, about 4% lauric-coconut diethanolamide, about 0.4% citric acid and about 65.6% of a shaving cream base comprising a mixture of about 7% stearic acid, 3% potassium hydroxide, 1% sodium hydroxide, 1% coconut oil fatty acids and water: the first compartment being pressurized with n-butane and the second compartment being pressurized with a mixture of isobutane and propane.

2. A package containing a self-heating shaving composition composed of two discrete parts adapted to be dispensed as a pressure-propelled heated shaving cream at time of use, one of said parts comprising a liquid medium containing sodium borohydride, said liquid medium being one in which said borohydride is soluble and stable and being selected from the group consisting of alkali metal hydroxide-stabilized water solutions, dimethyl ethers of mono-, di-, tri- and tetra-ethylene glycols, alcohols having 3–8 carbon atoms, isopropyl amine and dimethyl formamide, the other of said parts comprising a reducible material adapted to react exothermically with said borohydride on contact therewith, said reducible material being selected from the group consisting of glyceraldehyde, hexanal, crotonaldehyde, 2-methylpropenal, benzaldehyde, and furfural, and a shaving cream in which one of said parts is incorporated, said shaving cream being stable and being non-reactive with any other ingredients, each of said parts to be dispensed from pressure-tight dispensers containing a liquified propellant gas under pressure and having a common discharge means for simultaneously discharging and commingling said parts on activation thereof, whereby on such activation said parts combine and interact exothermically to issue as a pressure-propelled self-heated shaving cream ready for use.

3. A package according to claim 2 in which the reducible material is glyceraldehyde.

4. A package containing a self-heating shaving composition composed of two parts adapted to be dispensed as a pressure-propelled heated shaving cream at time of use, one part comprising a stable suspension of particulate sodium borohydride having a particle size from about 10 microns to less than 45 microns and a liquified, paraffinic hydrocarbon selected from the group consisting of mineral oil, paraffin oil, white mineral oil and liquid petrolatum hydrocarbons, and the second part comprising a shaving cream having incorporated therein a reducible material capable of reacting exothermically with said borohydride on contact therewith, said reducible material being glyceraldehyde, said shaving cream being stable and being non-reactive with the reducible material, each of said parts adapted to be dispensed from pressure tight dispensers containing a liquified propellant gas under pressure and having a common discharge means for simultaneous discharging and commingling said parts on activation thereof, whereby on such activation said parts combine and interact exothermically to issue as a pressure propelled heated shaving cream ready for use.

5. A package containing an aqueous cosmetic composition having a shaving cream base, said package having two compartments for separate storage of ingredients of said composition from which the ingredients are adapted to be dispensed for mixing with each other with the generation of heat, the composition in the first compartment containing about 9% of sodium borohydride with the balance being about 18% water, about 0.4% sodium hydroxide, about 6% lauric-coconut diethanolamide, and about 66.6% paraffin oil, and the composition in the second compartment containing about 13% of glyceraldehyde as a reducible material capable of reacting exothermically with said borohydride on contact therewith, the balance being shaving cream with citric acid to modify the pH, the compartments being pressurized with a liquified mixture of isobutane and propane gas under pressure to effect discharge of said compositions, and a common discharge means for simultaneously discharging and commingling the compositions in both compartments on activation thereof, whereby said compositions combine and interact exothermically to issue as a self-heated shaving cream ready for use.

* * * * *